US012668577B2

(12) United States Patent
Zeng et al.

(10) Patent No.: US 12,668,577 B2
(45) Date of Patent: Jun. 30, 2026

(54) COMPOUNDS, COMPOSITIONS, AND METHODS FOR ISOLATION OF NUCLEIC ACIDS

(71) Applicant: Promega Corporation, Madison, WI (US)

(72) Inventors: Zhiyang Zeng, San Luis Obispo, CA (US); Wenhui Zhou, San Luis Obispo, CA (US); Douglas R. Storts, Madison, WI (US); Poncho Meisenheimer, Madison, WI (US); Ian Marozas, San Luis Obispo, CA (US); Andrew Taft, Madison, WI (US); Spencer Hermanson, Madison, WI (US); Connor Fitzgerald, Madison, WI (US); Kasen Riemersma, Madison, WI (US)

(73) Assignee: Ptomega Corporation, Madison, WI (US)

( * ) Notice: Subject to any disclaimer, the term of this patent is extended or adjusted under 35 U.S.C. 154(b) by 528 days.

(21) Appl. No.: 18/137,896

(22) Filed: Apr. 21, 2023

(65) Prior Publication Data

US 2023/0382875 A1 Nov. 30, 2023

Related U.S. Application Data

(60) Provisional application No. 63/333,813, filed on Apr. 22, 2022.

(51) Int. Cl.

| | |
|---|---|
| ***C12N 15/10*** | (2006.01) |
| ***C07D 223/14*** | (2006.01) |
| ***C07D 249/16*** | (2006.01) |
| ***C07D 263/04*** | (2006.01) |
| ***C07D 265/30*** | (2006.01) |
| ***C07D 279/06*** | (2006.01) |
| ***C12Q 1/686*** | (2018.01) |

(52) U.S. Cl.

CPC ......... *C07D 265/30* (2013.01); *C07D 223/14* (2013.01); *C07D 249/16* (2013.01); *C07D 263/04* (2013.01); *C07D 279/06* (2013.01); *C12N 15/1013* (2013.01); *C12Q 1/686* (2013.01)

(58) Field of Classification Search

CPC ........................ C12N 15/1006; C12N 15/1013

See application file for complete search history.

(56) References Cited

U.S. PATENT DOCUMENTS

| | | | | |
|---|---|---|---|---|
| 4,672,003 | A * | 6/1987 | Letoffe | C08L 83/04 528/901 |
| 6,270,970 | B1 | 8/2001 | Smith et al. | |
| 6,310,199 | B1 | 10/2001 | Smith et al. | |
| 6,914,137 | B2 | 7/2005 | Baker | |
| 2001/0018513 | A1 | 8/2001 | Baker | |

(Continued)

OTHER PUBLICATIONS

International Search Report for PCT/US2023/019451 mailed Aug. 11, 2023, 13 Pages.

(Continued)

*Primary Examiner* — Andrea Olson

(74) *Attorney, Agent, or Firm* — Casimir Jones, S.C.; Anne M. Reynolds

(57) ABSTRACT

Provided herein are compounds, compositions, and methods for rapid isolation of nucleic acids from a sample.

20 Claims, 8 Drawing Sheets

(56) References Cited

U.S. PATENT DOCUMENTS

| | | | | |
|---|---|---|---|---|
| 2002/0076835 | A1* | 6/2002 | Ede | C07K 1/22<br>436/531 |
| 2019/0226007 | A1 | 7/2019 | Martin et al. | |
| 2020/0039943 | A1* | 2/2020 | Veiseh | C07D 401/12 |
| 2025/0129358 | A1* | 4/2025 | Zeng | C07F 7/1804 |

OTHER PUBLICATIONS

Zhou et al. "Redox active mesoporous hybrid materials by in situ syntheses with urea-linked triethoxysilylated phenothiazines." Chem Asian J. Sep. 3, 2010;5(9):2001-15.

"ChargeSwitch Nucleic Acid Purification Technology—US." Www.thermofisher.com, www.thermofisher.com/us/en/home/brands/product-brand/chargeswitch.html. Retrieved Jun. 6, 2024.

* cited by examiner

Imidazole (IM)

Morpholine (MO)

Methylpiperazine (MP)

Primary Amine (AM)

Dimethyl Amine (DA)

Dihydroxylethyl amine (DHA)

Methyl-PEG$_2$-Amine (MPA)

COMPOUNDS, COMPOSITIONS, AND METHODS FOR ISOLATION OF NUCLEIC ACIDS

CROSS-REFERENCE TO RELATED APPLICATIONS

This application claims priority to and the benefit of U.S. Provisional Patent Application No. 63/333,813, filed on Apr. 22, 2022, which is incorporated herein by reference in its entirety.

FIELD

Provided herein are compounds, compositions, and methods for rapid isolation of nucleic acids from a sample.

BACKGROUND

Isolation of nucleic acids from samples is a key step in many biochemical and diagnostic procedures, such as those that rely on nucleic acid amplification or sequencing reactions. Although compositions and methods for isolating nucleic acids from samples are available, many are time-consuming and/or involve use of components, such as chaotropic reagents, salts, surfactants, and organic solvents, that are incompatible with downstream applications (e.g., sequencing reactions).

SUMMARY

In one aspect, disclosed herein is a composition comprising:

a solid surface;

a linker covalently attached to the solid surface; and a moiety of formula (I) covalently attached to the linker:

(I)

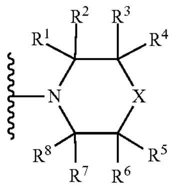

wherein:

X is selected from O, S, S(O), and $S(O)_2$;

$R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, —$NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl.

In some embodiments, the solid surface comprises a material selected from silica, glass, a polymer, and a metal. In some embodiments, the solid surface comprises a polymer selected from cellulose, cellulose acetate, nitrocellulose, nylon, a polyester, a polyethylene, a polyethersulfone, a polyolefin, polyvinylidene fluoride, a polyacrylate, a polystyrene, or any combination thereof. In some embodiments, the solid surface is in the form of a bead, a resin, a magnetic particle, a membrane, a vial, a plate, a film, a tube, a syringe, a cartridge, a cassette, a pipette tip, a microfluidic cartridge, or a cuvette.

In some embodiments, the linker comprises one or more methylene, ether, ester, amide, carbamate, carbonate, urea, thioether, thioester, thioamide, thiocarbamate, thiocarbonate, thiourea, arylene, heteroarylene, or heterocyclylene moieties, or any combination thereof. In some embodiments, the linker comprises one or more —$CH_2$—, —O—, —C(O)O—, —C(O)NH—, —NHC(O)O—, —OC(O)O—, —NHC(O)NH—, —S—, —C(O)S—, —C(S)NH—, —NHC(S)O—, —OC(S)O—, —NHC(S)NH—, arylene, heteroarylene, or heterocyclylene moieties, or any combination thereof.

In some embodiments, the linker comprises a moiety selected from:

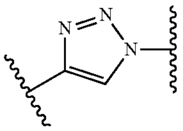,
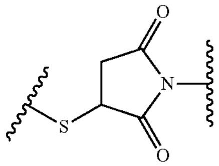,

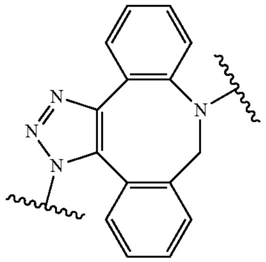,

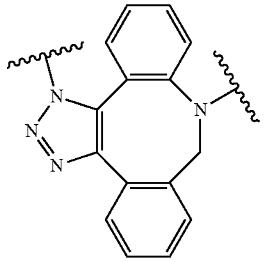,

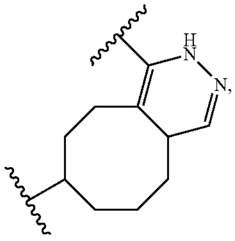,

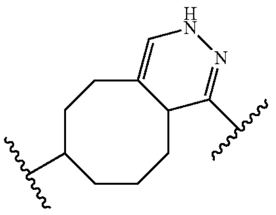,

-continued

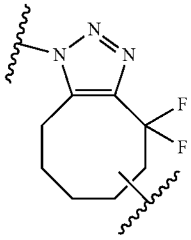
,
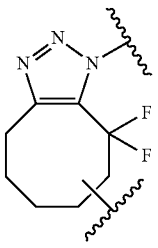
, and
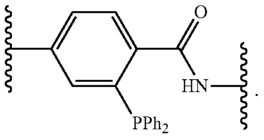

In some embodiments, the linker has a structure:

$$-(CH_2)_{n1}-Z-(CH_2)_{n2}-$$

wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S)NH—, —O—, —C(O)O—, and a bond.

In some embodiments, the linker is selected from:

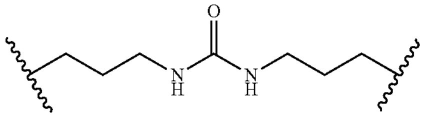
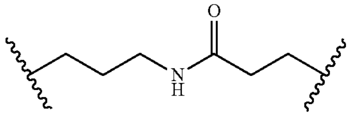
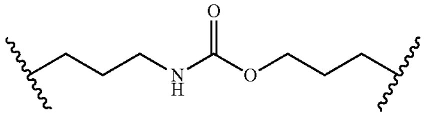
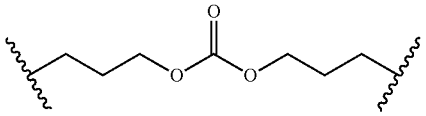
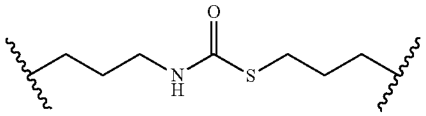
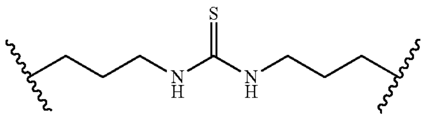
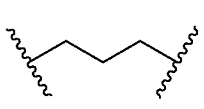
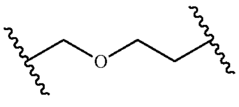
and
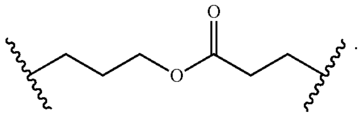

In some embodiments, the linker has a structure:

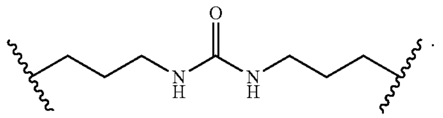 [SMILES: *CCCNC(=O)NCCC*]

In some embodiments, X is O. In some embodiments, $R^1$, $R^2$, $R^3$, $R^4$, $R^5$, $R^6$, $R^7$, and $R^8$ are each hydrogen.

In some embodiments, the solid surface further comprises one or more additional moieties covalently bound to the surface. In some embodiments, the solid surface further comprises at least one polyethylene glycol (PEG) moiety covalently bound to the surface.

In another aspect, disclosed herein is a method of isolating a nucleic acid from a sample, comprising:

(a) providing a sample containing a nucleic acid;

(b) contacting the sample with a composition disclosed herein (e.g., a composition disclosed herein, e.g., a composition comprising: a solid surface; a linker covalently attached to the solid surface; and a moiety of formula (I) covalently attached to the linker) at a pH of less than about 8.0, wherein the nucleic acid binds to the composition to provide a nucleic acid bound composition; and (c) separating the nucleic acid bound composition from the sample.

In some embodiments, step (b) is conducted at a pH of about 2.0 to less than about 8.0. In some embodiments, step (b) is conducted at a pH of about 6.0 to about 7.5. In some embodiments, step (b) comprises contacting the sample with the composition for about 10 seconds to about 10 minutes. In some embodiments, step (b) comprises contacting the sample with the composition for about 1 minute to about 5 minutes.

In some embodiments, the method further comprises one or more steps of washing the nucleic acid bound composition after step (c) by contacting the composition with a wash solution having a pH of less than about 8.0.

In some embodiments, the method further comprises a step of contacting the nucleic acid bound composition with an elution solution at a pH of about 8.5 or higher, to release the nucleic acid from the composition. In some embodiments, the elution solution comprises an aqueous buffer. In some embodiments, the method further comprises contacting the nucleic acid bound composition with the elution solution at a pH of about 8.5 to about 9.5. In some embodiments, the method further comprises contacting the nucleic acid bound composition with the elution solution at a pH of about 8.5 to about 9.0. In some embodiments, the method further comprises contacting the nucleic acid bound composition with the elution solution for about 10 seconds to about 10 minutes. In some embodiments, the method further comprises contacting the nucleic acid bound composition with the elution solution for about 1 minute to about 5 minutes.

In some embodiments, the method further comprises performing a polymerase chain reaction on the nucleic acid bound composition.

In some embodiments, the sample comprises a body fluid. In some embodiments, the body fluid is selected from blood, saliva, lymph, milk, mucus, urine, sweat, amniotic fluid, cerebrospinal fluid, feces, a vaginal secretion, and semen. In some embodiments, the sample comprises cultured cells, tissue cells, or cells from a body fluid (e.g., blood, saliva, lymph, milk, mucus, urine, sweat, amniotic fluid, cerebrospinal fluid, feces, a vaginal secretion, or semen). In some embodiments, the sample is a blood sample selected from whole blood, plasma, and serum. In some embodiments, the sample is an environmental sample selected from soil and water. In some embodiments, the sample is a food sample (e.g., a meat sample). In some embodiments, the sample is a plant (e.g., a vegetable). In some embodiments, the sample comprises a virus, bacteria, a fungus (e.g., a yeast or a mold), or any combination thereof. In some embodiments, the sample comprises media from cultured cells, a cell lysate, a cell supernatant, or a purified fraction of a cell (e.g., a subcellular fraction).

In some embodiments, the method comprises a step of lysing the sample prior to step (b).

In some embodiments, the nucleic acid is DNA. In some embodiments, the DNA is selected from total DNA, mtDNA (mitochondrial DNA), gDNA (genomic DNA), cfDNA (cell-free DNA), ccfDNA (circulating cell-free DNA), cffDNA (cell free fetal DNA), bacterial DNA, viral DNA, and ctDNA (circulating tumor DNA). In some embodiments, the nucleic acid is RNA. In some embodiments, the RNA is selected from total RNA, miRNA, mRNA, tRNA, rRNA, siRNA, ctRNA (circulating tumor RNA), and viral RNA. In some embodiments, the nucleic acid is total nucleic acids from the sample.

In another aspect, disclosed herein is a compound of formula (IIa):

(IIa)

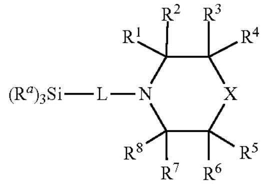

or a salt thereof, wherein:

X is selected from O, S, S(O), and $S(O)_2$;

L is a linker;

each $R^a$ is independently selected from hydroxy, $C_1$-$C_6$ alkoxy, and halo; and $R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, $NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl.

In some embodiments, X is O. In some embodiments, each $R^a$ is $C_1$-$C_6$ alkoxy. In some embodiments, $R^1$, $R^2$, $R^3$, $R^4$, $R^5$, $R^6$, $R^7$, and $R^8$ are each hydrogen.

In some embodiments, the linker comprises one or more methylene, ether, ester, amide, carbamate, carbonate, urea, thioether, thioester, thioamide, thiocarbamate, thiocarbonate, thiourea, arylene, heteroarylene, or heterocyclylene moieties, or any combination thereof. In some embodiments, the linker comprises one or more —$CH_2$—, —O—, —C(O)O—, —C(O)NH—, —NHC(O)O—, —OC(O)O—, —NHC(O)NH—, —S—, —C(O)S—, —C(S)NH—, —NHC(S)O—, —OC(S)O—, —NHC(S)NH—, or any combination thereof.

In some embodiments, L comprises a moiety selected from:

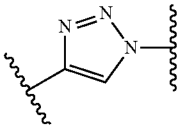
,
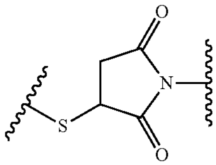
,

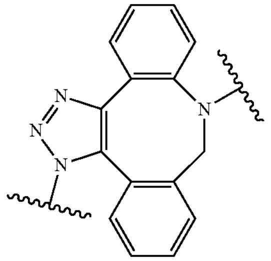
,

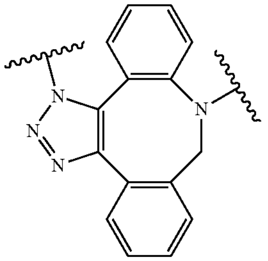
,

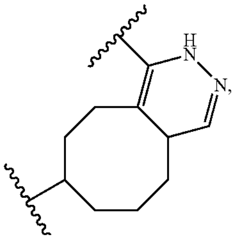
,

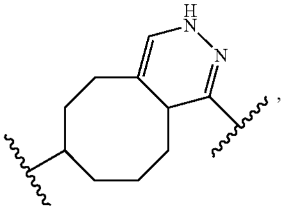
,

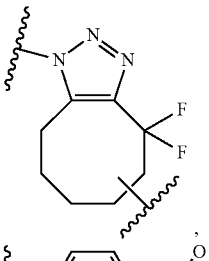
,
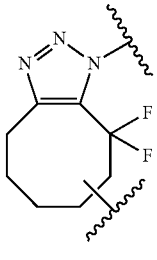
, and

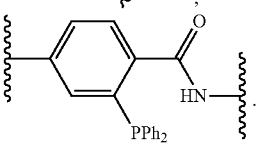
.

In some embodiments, L has a formula:

$$—(CH_2)_{n1}—Z—(CH_2)_{n2}—$$

wherein n1 and n2 are each independently selected from 1, 2, 3, 4, 5, 6, 7, and 8, and Z is selected from —NHC(O)

NH—, —C(O)NH—, —OC(O)NH—, —OC(O)O—, —NHC(O)S—, —NHC(S)NH—, —O—, —C(O)O—, and a bond.

In some embodiments, L has a structure selected from:

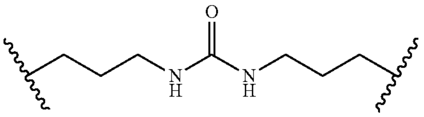

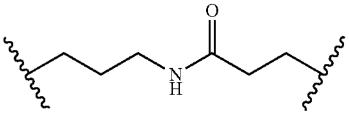

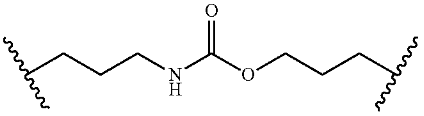

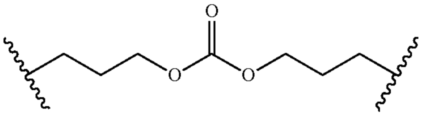

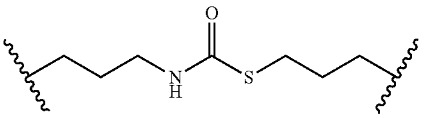

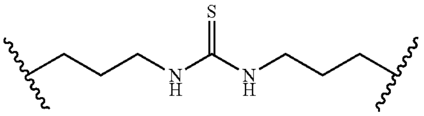

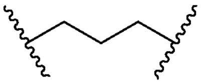

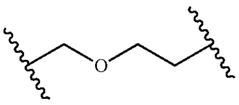

and

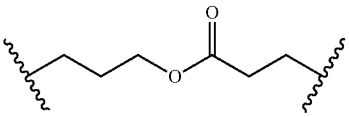

.

In some embodiments, L has a structure:

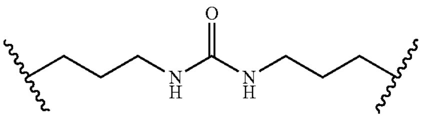

.

DETAILED DESCRIPTION

Figure 1:
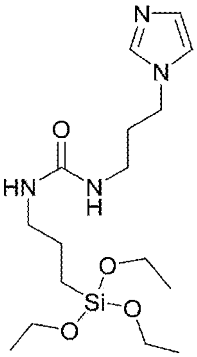
FIG. 1 shows structures of various amine-containing silane ligands.
Figure 1:
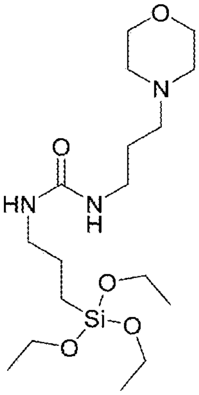
Figure 1:
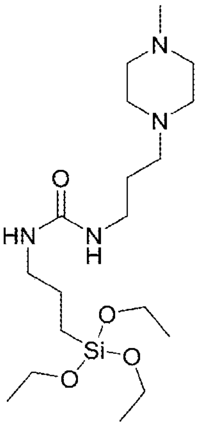
Figure 1:
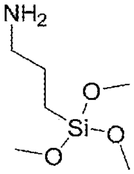
Figure 1:
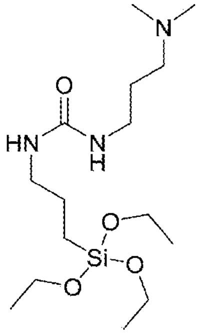
Figure 1:
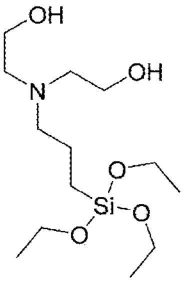
Figure 1:
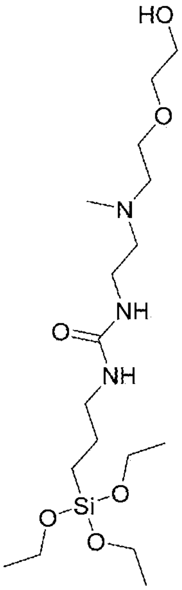

Provided herein are compounds, compositions, and methods for rapid isolation of nucleic acids from a sample. The compounds and compositions allow for rapid capture of nucleic acids at low pH (e.g., less than about 8). Upon a shift to a higher pH (e.g., about 8.5 or above), nucleic acids are rapidly released into solution. In some embodiments, the entire process can be conducted in less than 10 minutes, and the nucleic acids can be released under conditions that are compatible with downstream applications such as polymerase chain reaction (PCR), including reverse transcription PCR (RT-PCR).

I. Definitions

Although any methods and materials similar or equivalent to those described herein can be used in the practice or testing of embodiments described herein, some preferred methods, compositions, devices, and materials are described herein. However, before the present materials and methods are described, it is to be understood that this disclosure is not limited to the particular molecules, compositions, methodologies, or protocols as herein described as these may vary in accordance with routine experimentation and optimization. It is also to be understood that the terminology used in the description is for the purpose of describing the particular versions or embodiments only and is not intended to limit the scope of the embodiments described herein.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein and in the appended claims, the singular forms "a", "an", and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc., without the exclusion of the presence of additional feature(s), element(s), method step(s), etc. Conversely, the term "consisting of" and linguistic variations thereof, denotes the presence of recited feature(s), element(s), method step(s), etc., and excludes any unrecited feature(s), element(s), method step(s), etc., except for ordinarily-associated impurities. The phrase "consisting essentially of" denotes the recited feature(s), element(s), method step(s), etc., and any additional feature(s), element(s), method step(s), etc., that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "alkyl" refers to a straight or branched saturated hydrocarbon chain. The alkyl chain can include, e.g., from 1 to 30 carbon atoms ($C_1$-$C_{30}$ alkyl), 1 to 24 carbon atoms ($C_1$-$C_{24}$ alkyl), for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkenyl" refers to a straight or branched hydrocarbon chain containing at least one carbon-carbon double bond. The double bond(s) may be located at any position with the hydrocarbon chain. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkynyl" refers to a straight or branched hydrocarbon chain containing at least one carbon-carbon triple bond. The triple bond(s) may be located at any position with the hydrocarbon chain. Representative examples of alkynyl include, but are not limited to, ethynyl, propynyl, and butynyl.

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "cyano" refers to a group —CN.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "haloalkyl" refers to an alkyl group, as defined herein, in which at least one hydrogen atom (e.g., one, two, three, four, five, six, seven or eight hydrogen atoms) is replaced with a halogen. In some embodiments, each hydrogen atom of the alkyl group is replaced with a halogen. Representative examples of haloalkyl include, but are not limited to, fluoromethyl, difluoromethyl, trifluoromethyl, 2,2,2-trifluoroethyl, and 3,3,3-trifluoropropyl.

As used herein, the term "heteroaryl" refers to an aromatic group having a single ring (monocyclic) or multiple rings (bicyclic or tricyclic) having one or more ring heteroatoms independently selected from O, N, and S. The aromatic monocyclic rings are five- or six-membered rings containing at least one heteroatom independently selected from O, N, and S (e.g., 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan,hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

As used herein, the term "nitro" refers to a group —$NO_2$.

As used herein, the term "sample" is used in its broadest sense. In one sense, it is meant to include a specimen or culture obtained from any source as well as biological and environmental samples. Biological samples may be obtained from animals (including humans) and encompass fluids, solids, tissues, and gases. Biological samples include blood products such as plasma, serum, and the like. Sample may also refer to cells or cell lysates. Cell lysates may include cells that have been lysed with a lysing agent or lysates such as rabbit reticulocyte or wheat germ lysates. Environmental samples include environmental material such as surface matter, soil, water (e.g., wastewater), crystals, and industrial samples. Sample may also include purified samples, such as purified protein samples. Such examples are not however to be construed as limiting the sample types applicable to the present disclosure.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable substituent group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

represents a point of attachment of one moiety to another moiety (e.g., a substituent group to the rest of the compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—, and —OC(O)NH— also optionally recites —NHC(O)O—.

II. Compositions and Compounds

Provided herein are compounds and compositions that can be used to rapidly isolate nucleic acids from samples. The compounds and compositions include a morpholino moiety or a derivative thereof. At lower pH (e.g., less than about 8), the morpholine moieties are protonated and positively charged, and thus can rapidly bind negatively charged nucleic acids. Upon a shift to higher pH (e.g., about 8.5 or higher), the morpholine moieties are deprotonated such that the nucleic acids are rapidly released into solution. The disclosed compositions include morpholino moieties, or derivatives thereof (e.g., morpholine, thiomorpholine, thiomorpholine 1-oxide, thiomorpholine 1,1-dioxide, or salts thereof) that are attached via a linker to a solid surface. Although similar materials with other ligands such as imidazole, methylpiperazine, and other primary and secondary amines can also bind nucleic acids, the compositions including morpholine groups (or derivatives thereof) can rapidly release high quantities of the nucleic acids (e.g., in some embodiments, at least 80% of bound nucleic acids can be released in less than 5 minutes, or less than 1 minute). This provides a significant advantage to the disclosed materials. Furthermore, the nucleic acids can be released using elution solutions that do not require components (e.g., chaotropic agents) that can disrupt downstream applications, such as sequencing reactions. Accordingly, the disclosed compounds and compositions can be used for rapid and efficient isolation of nucleic acids to provide a solution that can be used directly in downstream applications without further sample processing.

Accordingly, disclosed herein are compositions comprising: a solid surface; a linker covalently attached to the solid surface; and a moiety of formula (I) covalently attached to the linker:

(I)

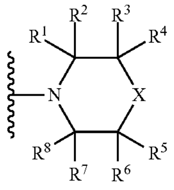

wherein:

X is selected from O, S, S(O), and $S(O)_2$;

$R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, $NR^hC(O)NR^iR^j$, and —$NR^hC(S)NR^iR^j$ wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl.

In the moiety of formula (I), X is selected from O, S, S(O), and $S(O)_2$. In some embodiments, X is O. In some embodiments, X is S. In some embodiments, X is S(O). In some embodiments, X is $S(O)_2$.

In the moiety of formula (I), $R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, —$NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl. In some embodiments, $R^1$, $R^2$, $R^3$, $R^4$, $R^5$, $R^6$, $R^7$, and $R^8$ are each independently selected from hydrogen, $C_1$-$C_3$ alkyl, halo, and —$OR^a$, wherein $R^a$ is selected from hydrogen and $C_1$-$C_3$ alkyl. In some embodiments, one or two of $R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, —$NR^hC(O)NR^iR^j$, and —$NR^hC(S)NR^iR^j$, and the rest are hydrogen. In some embodiments, one or two of $R^1$, $R^2$, $R^3$, $R^4$, $R^5$, $R^6$, $R^7$, and $R^8$ are each independently selected from hydrogen, $C_1$-$C_3$ alkyl, halo, and —$OR^a$, wherein $R^a$ is selected from hydrogen and $C_1$-$C_3$ alkyl, and the rest are hydrogen. In some embodiments, $R^1$, $R^2$, $R^3$, $R^4$, $R^5$, $R^6$, $R^7$, and $R^8$ are each hydrogen.

Any solid surface suitable for isolating nucleic acids can be used. For example, in some embodiments, the solid surface comprises a material selected from silica, glass, a polymer, and a metal. In some embodiments, the solid surface is a glass surface. In some embodiments, the solid surface comprises silica. In some embodiments, the solid surface comprises a polymer, such as a polymer selected from cellulose, cellulose acetate, nitrocellulose, nylon, a polyester, a polyethylene, a polyethersulfone, a polyolefin, polyvinylidene fluoride, a polyacrylate, a polystyrene, or any combination thereof. The solid surface can be in the form of, for example, a bead, a resin, a magnetic particle, a membrane, a vial, a plate, a film, a tube, a syringe, a cartridge, a cassette, a pipette tip, a microfluidic cartridge, or a cuvette. In some embodiments, the solid surface is in the form of a bead. In some embodiments, the solid surface is in the form of a resin. In some embodiments, the solid surface is in the form of a membrane. In some embodiments, the solid surface is in the form of a plate. In some embodiments, the solid surface is in the form of a pipette tip. In some embodiments, the solid surface is in the form of a microfluidic cartridge.

In the compositions, the moiety of formula (I) is attached to the solid surface via a linker. In some embodiments, the linker is a direct bond. In other embodiments, the linker separates the moiety of formula (I) from the solid surface by about 5 Å, about 10 Å, about 20 Å, about 50 Å, about 100 Å, about 150 Å, about 200 Å, about 300 Å, about 400 Å, about 500 Å, about 600 Å, about 700 Å, about 800 Å, about 900 Å, about 1000 Å, or any suitable range therebetween (e.g., about 5-100 Å, about 50-500 Å, about 150-700 Å, etc.). In some embodiments, the linker separates the functional element from the rest of the compound of formula (I) by about 1-200 atoms (e.g., about 1, about 2, about 3, about 4, about 5, about 6, about 7, about 8, about 9, about 10, about 15, about 20, about 25, about 30, about 35, about 40, about 45, about 50, about 60, about 70, about 80, about 90, about 100, about 120, about 140, about 160, about 180, about 200, or any suitable ranges therebetween (e.g., about 2-20, about 10-50, etc.)).

The linker can include one or more groups independently selected from methylene (—$CH_2$—), ethylene (—CH═CH—), ethynylene (—C≡C—), ether (—O—), amine (—NR—, wherein R is hydrogen or an alkyl group), thioether (—S—), carbonyl (—C(O)—), thiocarbonyl (—C(S)—), sulfonyl (—$S(O)_2$—), arylene, heteroarylene, and heterocyclylene moieties, or any combination thereof. For example, the above moieties can be combined to form additional groups that may be included in the linker, e.g., a carbonyl group and an ether group can together provide an ester moiety (—C(O)O—); a carbonyl group and two ether groups can together provide a carbonate moiety (—OC(O)O—); a carbonyl group and an unsubstituted amine group can together provide an unsubstituted amide moiety (—C (O)NH—); a carbonyl group and two unsubstituted amine groups can together provide an unsubstituted urea moiety (—NHC(O)NH—); a carbonyl group together with an unsubstituted amine group and an ester group can provide an unsubstituted carbamate moiety (—OC(O)NH—); a carbonyl group together with a thioether and an unsubstituted amine group can provide an S-thiocarbamate moiety; a thiocarbonyl group together with an ether and an unsubstituted amine group can provide an O-thiocarbamate moiety; multiple methylene groups can together form an alkylene chain; etc.

In some embodiments, the linker comprises one or more methylene, ether, ester, amide, carbamate, carbonate, urea, thioether, thioester, thioamide, thiocarbamate, thiocarbonate, thiourea, arylene, heteroarylene, or heterocyclylene moieties, or any combination thereof. In some embodiments, the linker comprises one or more $—CH_2—$, —O—, —C(O)O—, —C(O)NH—, —NHC(O)O—, —OC(O)O—, —NHC(O)NH—, —S—, —C(O)S—, —C(S)NH—, —NHC(S)O—, —OC(S)O—, —NHC(S)NH—, arylene, heteroarylene, or heterocyclylene moieties, or any combination thereof.

In some embodiments, the linker comprises one or more alkylene groups (e.g., $—(CH_2)_n—$, wherein n is 1-12, e.g., 1, 2, 3, 4, 5, 6, 7, 8, 9, 10, 11, or 12, or any suitable range therebetween). In some embodiments, the linker comprises one or more branched alkylene groups.

In some embodiments, the linker has a formula $—(CH_2)_{n1}—Z—(CH_2)_{n2}—$, wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S)NH—, —O—, —C(O)O—, and a bond.

In some embodiments, the linker has a formula $—(CH_2)_{n1}—NH—C(O)—NH—(CH_2)_{n2}—$, wherein n1 and n2 are each independently selected from 1, 2, 3, 4, 5, 6, 7, and 8.

In some embodiments, the linker has a formula selected from:

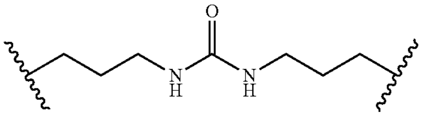

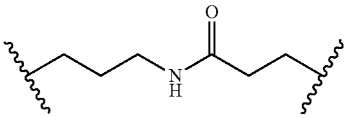

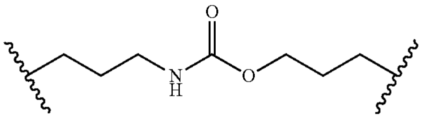

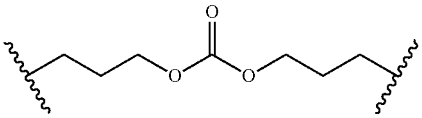

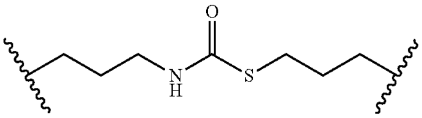

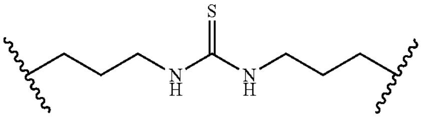

-continued

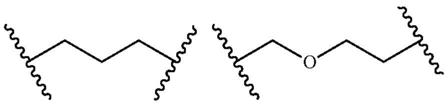

and

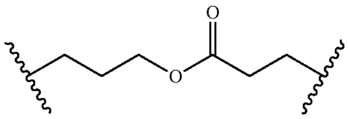

.

In some embodiments, the linker has a formula:

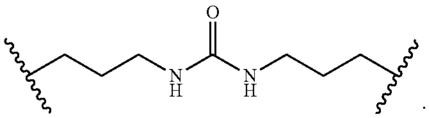 [SMILES: *CCCNC(=O)NCCC*]

.

In some embodiments, the linker can include one or more moieties that results from the reaction of two reactive groups, such as reactive groups known in various bioconjugation reactions. For example, the linker can include a triazole group, which is formed by the reaction of an azide and an alkyne. Exemplary moieties that may result from such reactions include, but are not limited to:

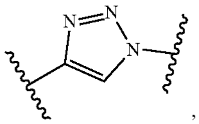

,

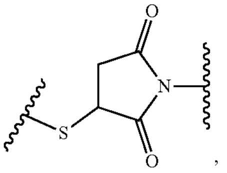

,

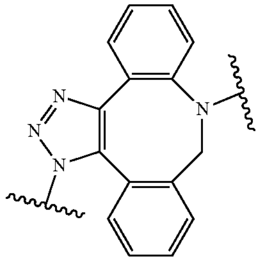

,

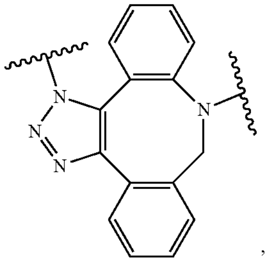

,

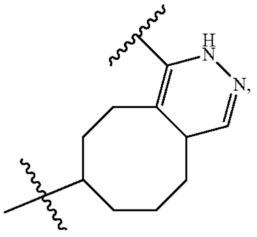

-continued

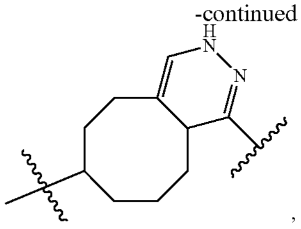

,

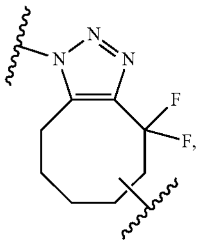

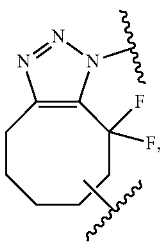

and

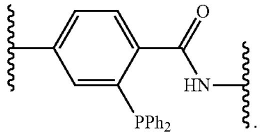

.

In some embodiments, the solid surface comprises one or more additional moieties, in addition to the moiety of formula (I). For example, the solid surface may be functionalized with additional ligands. In some embodiments, the solid surface further comprises one or more PEG ligands.

The compositions can be prepared by reacting a solid surface with a compound comprising a moiety of formula (I). Generally, the compound comprising the moiety of formula (I) will have a reactive group that is complementary to a reactive group present on the solid surface, to allow for covalent attachment. For example, a suitable solid surface can be reacted with a compound of formula (II):

(II)

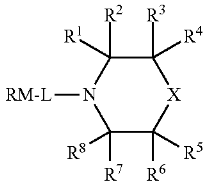

wherein RM is a reactive moiety, L is a linker, and X, $R^1$, $R^2$, $R^3$, $R^4$, $R^5$, $R^6$, $R^7$, and $R^8$ are as defined and described herein. In some embodiments, the reactive moiety comprises a group selected from a silane, an alkyne, an azide, an alkene, a thiol, a maleimide, an amine, a succinimidyl ester, a —COOH group, a tetrazole, an aryl phosphine, or the like. For example, in some embodiments, RM comprises a moiety selected from:

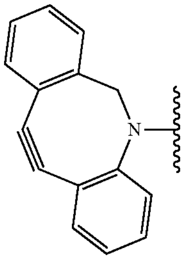

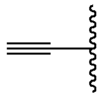

,

,

,

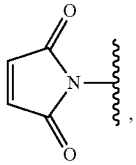

,

,

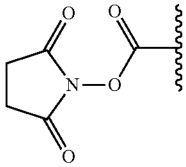

,

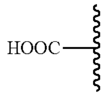

,

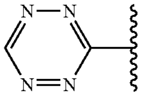

,

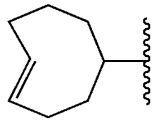

,

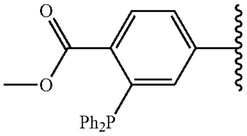

,

, and

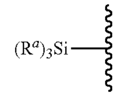

, wherein each $R^a$ is independently selected from hydroxy, $C_1$-$C_6$ alkoxy, and halo (e.g., fluoro, chloro, or bromo). A skilled artisan will appreciate that when a compound of formula (II) includes any of the above groups, the solid surface will be functionalized by a complementary reactive group. For example, when a compound of formula (II) includes a group that comprises an alkyne, the solid surface can be functionalized with an azide such that the compound of formula (II) can be attached to the solid surface via a click chemistry reaction (e.g., to form a triazole). Similarly, when a compound of formula (II) includes a succinimidyl ester group (i.e.,

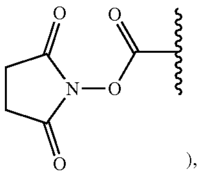

), the solid surface can be functionalized with a primary amine ($—NH_2$) such that the compound of formula (II) can be attached to the solid surface via an amide bond.

In compounds of formula (II), the group L can be any suitable linking group. For example, in some embodiments, L includes one or more groups independently selected from methylene ($—CH_2—$), ethylene (—CH═CH—), ethynylene (—C≡C—), ether (—O—), amine (—NH—), thioether (—S—), carbonyl (—C(O)—), thiocarbonyl (—C(S)—), sulfonyl ($—S(O)_2—$), arylene, heteroarylene, and heterocyclylene moieties, or any combination thereof. For example, the above moieties can be combined to form additional groups such as an ester, carbonate, amide, urea, thiourea, carbamate, alkylene, etc. In some embodiments, L comprises one or more alkylene groups (e.g., $—(CH_2)_n—$, wherein n is 1-12, e.g., 1, 2, 3, 4, 5, 6, 7, 8, 9, 10, 11, or 12, or any suitable range therebetween). In some embodiments, L comprises one or more branched alkylene groups.

In some embodiments, L has a formula —$(CH_2)_{n1}$—Z—$(CH_2)_{n2}$—, wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S)NH—, —O—, —C(O)O—, and a bond.

In some embodiments, L has a formula —$(CH_2)_{n1}$—NH—C(O)—NH—$(CH_2)_{n2}$—, wherein n1 and n2 are each independently selected from 1, 2, 3, 4, 5, 6, 7, and 8.

In some embodiments, L has a formula selected from:

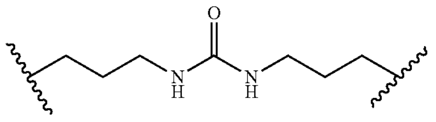

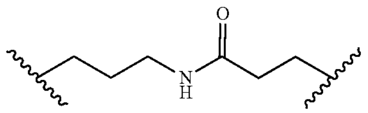

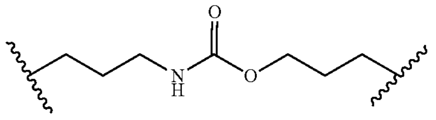

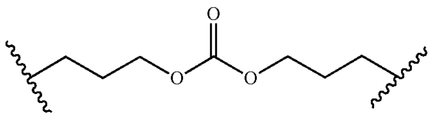

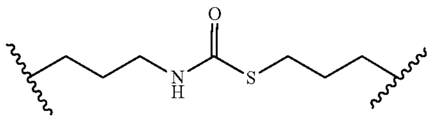

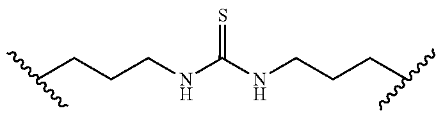

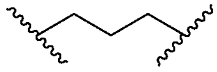

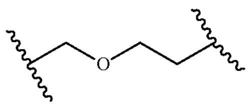 and

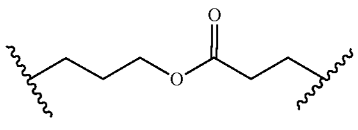

In some embodiments, L has a formula:

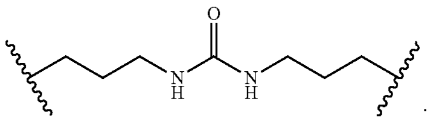 [SMILES: *CCCNC(=O)NCCC*]

In some embodiments, provided herein is a compound of formula (IIa):

(IIa)

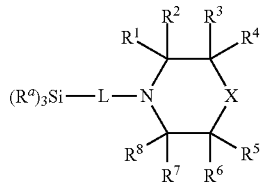

wherein L, X, $R^1$, $R^2$, $R^3$, $R^4$, $R^5$, $R^6$, $R^7$, $R^8$, and $R^a$ are as defined and described herein.

In one embodiment, provided herein is a compound of formula:

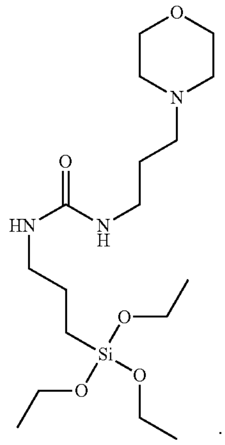 [SMILES: CCO[Si](CCCNC(=O)NCCCN1CCOCC1)(OCC)OCC]

III. Methods of Use

The compositions disclosed herein can be used to rapidly isolate nucleic acids (e.g., DNA and RNA) from samples, e.g., biological samples. In one aspect, the disclosure provides a method of isolating a nucleic acid from a sample, comprising:

(a) providing a sample containing a nucleic acid;

(b) contacting the sample with a composition disclosed herein (e.g., a composition comprising: a solid surface; a linker covalently attached to the solid surface; and a moiety of formula (I) covalently attached to the linker) at a pH of less than about 8.0, wherein the nucleic acid binds to the composition to provide a nucleic acid bound composition; and (c) separating the nucleic acid bound composition from the sample.

In some embodiments, the nucleic acids isolated from the sample are selected from DNA and RNA. In some embodiments, the nucleic acids isolated from the sample are DNA (e.g., genomic DNA (gDNA), plasmid DNA, cDNA, mitochondrial DNA (mtDNA), cosmid DNA, cell-free DNA (cfDNA), circulating cell-free DNA (ccfDNA), cell-free fetal DNA (cffDNA), bacterial DNA, viral DNA, circulating tumor DNA (ctDNA), total DNA, or the like). In some embodiments, the nucleic acids isolated from the sample are RNA, e.g., messenger RNA (mRNA), microRNA (miRNA), a pre-miRNA, ribosomal RNA (rRNA), mitochondrial RNA, non-coding RNA, circular RNA, small interfering RNA (siRNA), guide RNA, total RNA, or the like. In some embodiments, the nucleic acids isolated from the sample are total nucleic acids.

Any suitable samples containing nucleic acids can be used in the disclosed methods. In some embodiments, the sample comprises a body fluid, such as blood, saliva, lymph, milk, mucus, urine, sweat, amniotic fluid, cerebrospinal fluid, feces, a vaginal secretion, or semen. In some embodiments, the sample comprises cultured cells, tissue (e.g., fresh tissue or formalin-fixed paraffin embedded (FFPE) tissue), or cells from a body fluid. In some embodiments, the sample comprises a virus, bacteria, a fungus (e.g., yeast or mold), or any combination thereof. In some embodiments, the sample is a food sample, e.g., a meat sample. In some embodiments, the sample is a plant, e.g., a vegetable. In particular embodiments, the sample is a blood sample selected from whole blood, plasma, and serum. In some embodiments, the sample is an environmental sample, such as soil or water (e.g., wastewater). The methods can also be used to isolate a nucleic acid from other environments, such as an agarose or polyacrylamide gel, or a solution in which a target nucleic acid amplification has already been carried out.

In some embodiments, the method may further comprise a step of lysing the sample prior to contacting the sample with a composition disclosed herein. Any suitable method of lysing sample can be used, including osmotic lysis (i.e., using a hypotonic solution), enzymatic lysis (e.g., using lysozyme), chemical lysis (e.g., use of detergents such as non-ionic detergents or cationic detergents, with or without other components such as sodium hydroxide), physical lysis (e.g., by mechanical lysis such as blending, shaking with glass beads, use of a homogenizer or French press, use of a sonicator, freeze-thaw cycles, or mechanical grinding), or heat lysis, or any combination thereof.

The methods include a step of contacting the sample (e.g., a lysed sample) with a composition disclosed herein (e.g., a composition comprising a moiety of formula (I) as disclosed herein), such that the nucleic acids in the sample bind to the composition to provide a nucleic acid bound composition. During this contacting step, the pH if the sample is less than about 8.0, to ensure that the moiety of formula (I) in the composition is positively charged. In some embodiments, the contacting step is conducted at a pH of about 2.0 to about 8.0, about 2.5 to about 8.0, about 3.0 to about 8.0, about 3.5 to about 8.0, about 4.0 to about 8.0, about 4.5 to about 8.0, about 5.5 to about 8.0, or a pH of about 6.0 to about 7.5, e.g., a pH of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, or any range therebetween.

Nucleic acids bind rapidly to the compositions disclosed herein. For example, in some embodiments, greater than about 50% of the nucleic acids in the sample (e.g., greater than about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) bind to the composition within less than about 10 minutes (e.g., less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute). In some embodiments, greater than 75% of the nucleic acids in the sample (e.g., greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) bind to the composition within less than about 10 minutes (e.g., less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute). In some embodiments, greater than 75% of the nucleic acids in the sample (e.g., greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) bind to the composition within less than about 5 minutes (e.g. less than about 5 minutes, less than about 4 minutes, less than about 3 minutes, less than about 2 minutes, or less than about 1 minute). In some embodiments, greater than 75% of the nucleic acids in the sample (e.g., greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) bind to the composition within less than about 1 minute. Accordingly, although the step of contacting the sample with the composition can be conducted for longer periods of time if convenient or desired, in some embodiments, the contacting step is carried out for less than about 10 minutes (e.g., less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, or less than about 1 minute), as this time period is sufficient to allow for binding of the nucleic acids to the composition. In some embodiments, the contacting step is carried out for about 10 seconds to about 10 minutes, or about 1 minute to about 5 minutes. The contacting step results in production of a nucleic acid bound composition.

The methods optionally include one or more washing steps after the contacting step. I some embodiments, the methods further comprise contacting at least one wash solution with the nucleic acid bound composition. The wash solution is typically an aqueous solution (e.g., an aqueous buffer) optionally containing chemical additives, such as detergents, salts (e.g., NaCl), or an organic solvent (e.g., methanol, ethanol, isopropanol, acetonitrile, DMSO, or DMF), that has a pH of about 2.0 to about 8.0, about 2.5 to about 8.0, about 3.0 to about 8.0, about 3.5 to about 8.0, about 4.0 to about 8.0, about 4.5 to about 8.0, about 5.5 to about 8.0, or about 6.0 to about 7.5, such that the composition will remain protonated and the nucleic acid will remain bound, or aqueous while other contaminants will be washed away. In some embodiments, the wash solution is an aqueous buffer solution having a pH of about 2.0 to about 8.0, about 2.5 to about 8.0, about 3.0 to about 8.0, about 3.5 to about 8.0, about 4.0 to about 8.0, about 4.5 to about 8.0, about 5.5 to about 8.0, or about 6.0 to about 7.5, e.g., a pH of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, or any range therebetween.

After the contacting step and the optional washing step(s), the nucleic acids bound composition can be used in a number of different applications. In some embodiments, the nucleic acids are released from the nucleic acid bound composition, e.g., by contacting the nucleic acid bound composition with an elution solution having a pH of about 8.5 or higher, e.g., a pH of about 8.5 to about 9.5, e.g., a pH of about 8.5, about 8.6, about 8.7, about 8.8, about 8.9, about 9.0, about 9.1, about 9.2, about 9.3, about 9.4, about 9.4, or about 9.5, or any range therebetween. In some embodiments, the elution solution comprises a buffer, such as tris(hydroxymethyl)aminomethane (Tris), 4-(2-hydroxyethyl)-1-piperazineethanesulfonic acid (HEPES), 3-(N-morpholino) propane sulfonic acid (MOPS), or the like. The elution solution can include other components, such as salts, so long as those components are included in concentrations that will not interfere with downstream applications such as PCR. For example, in some embodiments, the elution solution comprises a salt (e.g., NaCl) in a concentration of less than about 25 nM.

A significant advantage of the disclosed composition is that it releases nucleic acids at a very rapid rate upon a shift to a higher pH. Although other compositions are capable of binding and releasing nucleic acids, including compositions similar to those described herein that have moiety different from those of formula (I) (e.g., an imidazole, a methylpiperazine, an amine (e.g., a primary amine ($—NH_2$) or a substituted amine (e.g., $—N(CH_3)_2$ or $—N(CH_2CH_2OH)_2$)), the compositions disclosed herein can release significant quantities of nucleic acids in a very short time frame. In some embodiments, contacting the nucleic acid bound composition with an elution solution having a pH of about 8.5 or higher results in release of more than 50% of the bound nucleic acids (e.g., greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) in less than about 5 minutes (e.g., less than about less than about 5 minutes, less than about 4 minutes, less than about 3 minutes, less than about 2 minutes, or less than about 1 minute). In some embodiments, contacting the nucleic acid bound composition with an elution solution having a pH of about 8.5 or higher results in release of more than 75% of the bound nucleic acids (e.g., greater than 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) in less than about 5 minutes (e.g., less than about less than about 5 minutes, less than about 4 minutes, less than about 3 minutes, less than about 2 minutes, or less than about 1 minute). This greatly reduces the processing time needed to isolate nucleic acids from samples. Accordingly, although the step of contacting the nucleic acid bound composition with the elution solution can be conducted for longer periods of time if convenient or desired, in some embodiments, this step is carried out for less than about 5 minutes, (e.g., less than about 5 minutes, less than about 4 minutes, less than about 3 minutes, less than about 2 minutes, or less than about 1 minute), as this time period is sufficient to allow for efficient release of the bound nucleic acids. In some embodiments, the step of contacting the nucleic acid bound composition with the elution solution is conducted for about 10 seconds to about 10 minutes, or about 1 minute to about 5 minutes.

In embodiments in which an elution solution is used, no chaotropic agent (e.g., guanidine hydrochloride or guanidine isothiocyanate), organic solvent (e.g., alcohols such as ethanol or methanol, or other organic solvents such as dimethylsulfoxide), or detergent (e.g., sodium dodecyl sulfate) in the elution solution. Even trace amounts of such components in a solution of target nucleic acid can severely limit the utility of the nucleic acid in downstream processing or analysis. This is another significant advantage of the disclosed compositions—the nucleic acids can be rapidly released from the compositions using aqueous buffer solutions that do not include components that would interfere with downstream applications.

When particular pH conditions are required in any of the method steps (e.g., the contacting step, optional washing steps, and the elution step), the pH of the sample or solution can be adjusted to the indicated pH value using an acidifying agent or a basifying agent, as required. Suitable acidifying agents include, but are not limited to: inorganic acids such as HCl, HBr, $HClO_4$, $HClO_3$, $H_2SO_4$, $H_2SO_3$, $H_3PO_4$, or $H_3PO_3$; organic acids such as 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, tetrafluoroboric, toluenesulfonic, trifluoroacetic, trifluoromethanesulfonic, and valeric acids. Suitable basifying agents include but are not limited to inorganic bases such as sodium hydroxide, potassium hydroxide, calcium hydroxide, sodium bicarbonate, sodium carbonate, ammonia, diethanolamine, meglumine, lysine, arginine, ethanolamine, piperazine, trometamol, triethanolamine, and the like.

In some embodiments, the nucleic acid bound composition can be used directly in a downstream application without an elution step. For example, in some embodiments, the nucleic acid bound composition can be used directly in an on-bead polymerase chain reaction.

In some embodiments, the isolated nucleic acid can be used in any number of downstream applications, such as methods that analyze or further process the nucleic acid. For example, in some embodiments, the disclosed methods further comprise a step of analyzing or processing the nucleic acid, e.g., using polymerase chain reaction (PCR), reverse transcription PCR (RT-PCR), quantitative PCR, quantitative reverse transcription PCR (RT-qPCR), real time PCR, hot start PCR, single cell PCR, nested PCR, in situ colony PCR, digital PCR (dPCR), Droplet Digital™ PCR (ddPCR), emulsion PCR, ligase chain reaction (LCR), transcription based amplification system (TAS), nucleic acid sequence-based amplification (NASBA), strand displacement amplification (SDA), rolling circle amplification (RCA), hyper-branched RCA (HRCA), isothermal amplification, gel electrophoresis, capillary electrophoresis, mass spectrometry, fluorescence detection, ultraviolet spectrometry, hybridization assays, DNA or RNA sequencing, reverse transcription, next generation sequencing (NGS), or the like.

IV. Examples

Abbreviations used in the Examples include the following: DCM is dichloromethane; DMF is dimethylformamide;

MeOH is methanol; MS is mass spectrometry; NMR is nuclear magnetic resonance; RT is room temperature; and THF is tetrahydrofuran.

Example 1

Synthesis of 1-(3-morpholinopropyl)-3-(3-(triethoxysilyl)propyl)urea 6.41 g of 3-morpholinopropylamine was added into 40 mL of anhydrous THF followed by slow addition of 10 mL 3-(triethoxysilyl)propyl isocyanate. The solution was heated up to reflux overnight. The solution was cooled to room temperature and purified by chromatography using a Teledyne ISCO system. The solvent system was DCM/MeOH, and the gradient was 0-20% MeOH in DCM. The compound was eluted out around 15% MeOH in DCM. The combined solution was rotovaped to remove the solvent to generate 9.5 g of viscous colorless liquid (60% yield). MS: 392.6 (M+H); $^1$H NMR (400 MHz, Methanol-$d_4$) 3.88-3.79 (m, 6H), 3.70 (d, J=5.1 Hz, 4H), 3.17 (t, J=7.0 Hz, 2H), 3.10 (t, J=7.0 Hz, 2H), 2.48 (s, 4H), 2.41 (t, J=7.6 Hz, 2H), 1.69 (p, J=7.2 Hz, 2H), 1.57 (p, J=7.4 Hz, 2H), 1.22 (td, J=7.1, 2.1 Hz, 9H), 0.62 (dd, J=9.8, 6.9 Hz, 2H).

Example 2

Synthesis of Morpholine Functionalized Magnetic Silica Beads

Figure 2:
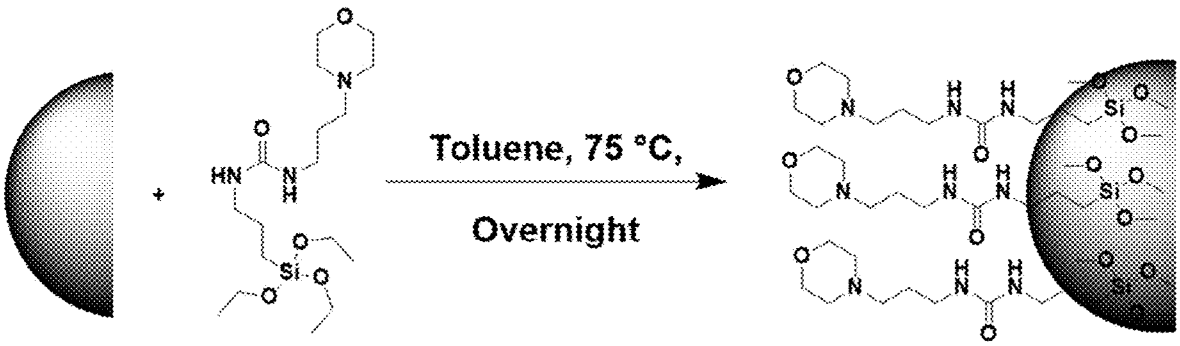
FIG. 2 shows a reaction scheme for functionalizing magnetic silica beads with an exemplary silane ligand.

An overview of this synthetic procedure is provided in FIG. 2. 1 g of Grace MP-50 magnetic silica particles (6 μm) was added to 50 mL of toluene. The suspension was stirred using an overhead mechanical stirrer at 200 rpm. 1-(3-morpholinopropyl)-3-(3-(triethoxysilyl)propyl)urea (783 mg) was dissolved in 2 mL DMF. The solution was added into the toluene suspension and stirred at RT for 30 min. The suspension was heated to 75° C. overnight. The particle was washed three times with DMF and three times with water. The particle was stored in nanopure water. CHN elemental analysis: C (1.53%), H (0.40%), and N (0.38%).

Example 3

Synthesis of Functionalized Magnetic Silica Beads 1 g of Grace MP-50 magnetic silica particles (6 μm) was added to 50 mL of toluene. The suspension was stirred using an overhead mechanical stirrer at 200 rpm. 1-(3-morpholinopropyl)-3-(3-(triethoxysilyl)propyl)urea (783 mg) was dissolved in 2 mL DMF. The solution was added into the toluene suspension. 500 μL of acetic acid was added as an additive to improve the ligand coupling efficiency. The suspension was stirred at RT for 30 min. The suspension was heated to 75° C. overnight. The particle was washed three times with DMF and three times with water. The particle was stored in nanopure water. CHN elemental analysis: C (6.48%), H (1.2%), and N (1.9%).

Additional magnetic silica beads were prepared according to an analogous procedure, using other amine-containing silane ligands in place of the 1-(3-morpholinopropyl)-3-(3-(triethoxysilyl)propyl)urea (i.e., using 1-(3-(1H-imidazol-1-yl)propyl)-3-(3-(triethoxysilyl)propyl)urea, 1-(3-(4-methylpiperazin-1-yl)propyl)-3-(3-(triethoxysilyl)propyl)urea, 3-(trimethoxysilyl)propan-1-amine, 1-(3-(dimethylamino)propyl)-3-(3-(triethoxysilyl)propyl)urea, 2,2'-(3-(triethoxysilyl)propyl)azanediyl)bis(ethan-1-ol), and 1-(2-((2-(2-hydroxyethoxy)ethyl)(methyl)amino)ethyl)-3-(3-(triethoxysilyl)propyl)urea, respectively).

Example 4

DNA Binding and Elution Assay 1 mg of various amine functionalized magnetic beads was added into 1 mL of 200 bp DNA solution (100 ng/mL, 10 mM PBS, pH 6.5). The suspension was mixed for 40 seconds. The particles were collected by a magnetic bar for 1 minute. The supernatant was collected to measure the DNA concentration remaining in the solution to calculate the binding percentage. A Quantifluor® dsDNA system (Promega) was used to quantify the DNA concentration. 50 μL of Tris buffer (10 mM, pH 9.0) was added into the magnetic particles, and the suspension was vortexed for 1 minute. The particles were collected by a magnetic bar. The elution solution was collected, and DNA concentration in the elution solution was quantified to calculate the elution percentage.

Figure 3:
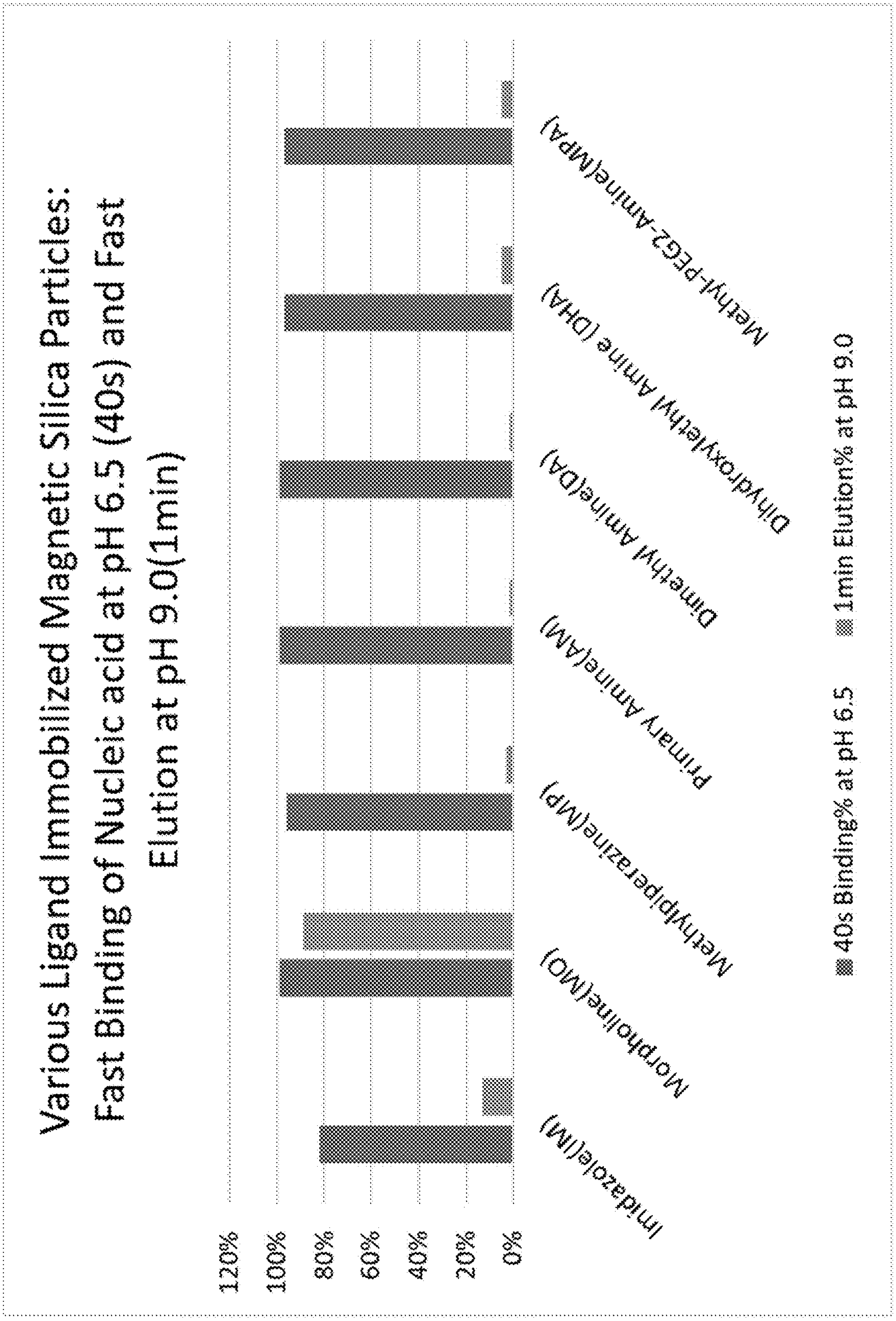
FIG. 3 shows DNA binding percentage and elution percentage from various amine-functionalized magnetic silica particles, with binding at pH 6.5 and elution at pH 9.0.

Results are shown in FIG. 3. While all of the particles rapidly bind DNA, the morpholine-functionalized magnetic beads released a much higher quantity of the DNA after the 1-minute elution step than the other materials.

Example 5

DNA Binding and Elution Assay 1 mg of various amine functionalized magnetic beads was added into 1 mL of 200 bp DNA solution (100 ng/ml, 10 mM PBS, pH 7.4). The suspension was mixed for 40 seconds. The particles were collected by a magnetic bar for 1 minute. The supernatant was collected to measure the DNA concentration remaining in the solution to calculate the binding percentage. A Quantifluor® dsDNA system (Promega) was used to quantify the DNA concentration. 50 μL of Tris buffer (10 mM, pH 9.0) was added into the magnetic particles, and the suspension was vortexed for 1 minute. The particles were collected by a magnetic bar. The elution solution was collected, and DNA concentration in the elution solution was quantified to calculate the elution percentage.

Figure 4:
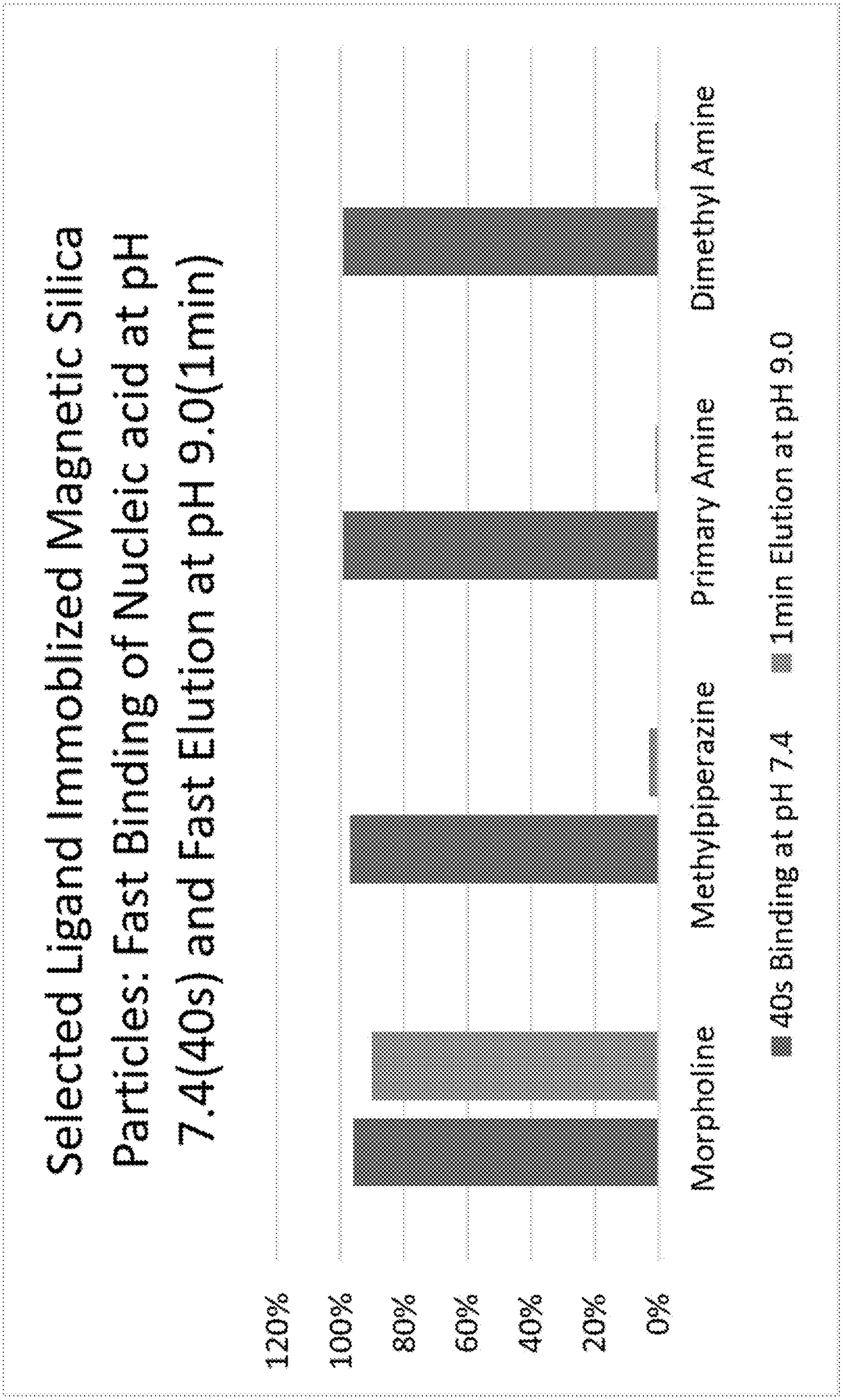
FIG. 4 shows DNA binding percentage and elution from various amine-functionalized magnetic silica particles, with binding at pH 7.4 and elution at pH 9.0.

Results are shown in FIG. 4. While all of the particles rapidly bind DNA, the morpholine-functionalized magnetic beads released a much higher quantity of the DNA after the 1-minute elution step than the other materials.

Example 6

DNA Binding and Elution Assay 1 mg of morpholine functionalized magnetic beads was added into 1 mL of 200 bp DNA solution with various pH and salt concentration (pH 5.8-pH 8.4; 0-600 mM NaCl). The suspension was mixed for 40 seconds. The particles were collected by a magnetic bar for 1 minute. The supernatant was collected to measure the DNA concentration remaining in the solution to calculate the binding percentage. A Quantifluor® dsDNA system (Promega) was used to quantify the DNA concentration. 50 μL of Tris buffer (10 mM, pH 9.0) was added into the magnetic particles, and the suspension was vortexed for 1 minute. The particles were collected by a magnetic bar. The elution solution was collected, and DNA concentration in the elution solution was quantified to calculate the elution percentage.

Figure 5:
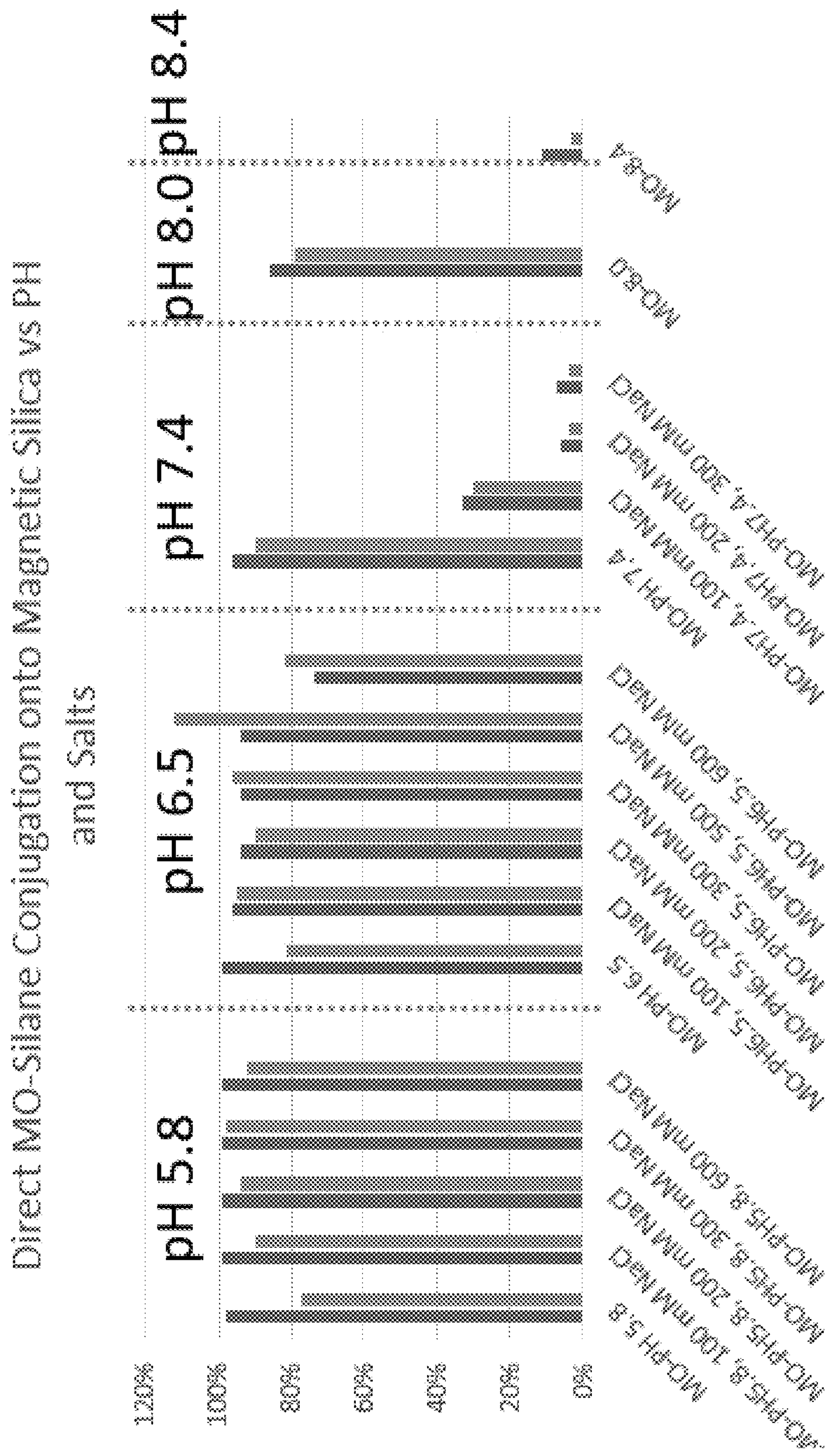
FIG. 5 shows DNA binding percentage and elution percentage from morpholine-functionalized magnetic silica particles at various binding pH values (5.8-8.4) and salt concentrations (O—600 mM NaCl), with elution at pH 9.0.

Results are shown in FIG. 5, and demonstrate that the morpholine-functionalized beads can work with a broad range of initial binding pHs and NaCl concentrations.

Example 7

DNA Binding and Elution Assay 1 mg of morpholine functionalized magnetic beads was added into 1 ml of total Human DNA (100, 10 or 1 ng) solution of Phosphate Buffered Saline (PBS) pH 7.0. The suspension was mixed for 60 seconds. The particles were collected by a magnetic bar for 1 minute. The supernatant was removed, 50 μL of Tris buffer (10 mM, pH 9.0) was added into the magnetic particles, and the suspension vortexed for 1 minute. The particles were collected by a magnetic bar. The elution solution was collected, and DNA concentration in the elution solution was quantified using probe-based quantitative real-time PCR (qPCR) to calculate the elution concentration. Beta-2-microglobulin probe and primers were used to compare the DNA solution input and the elution concentration.

Figure 6:
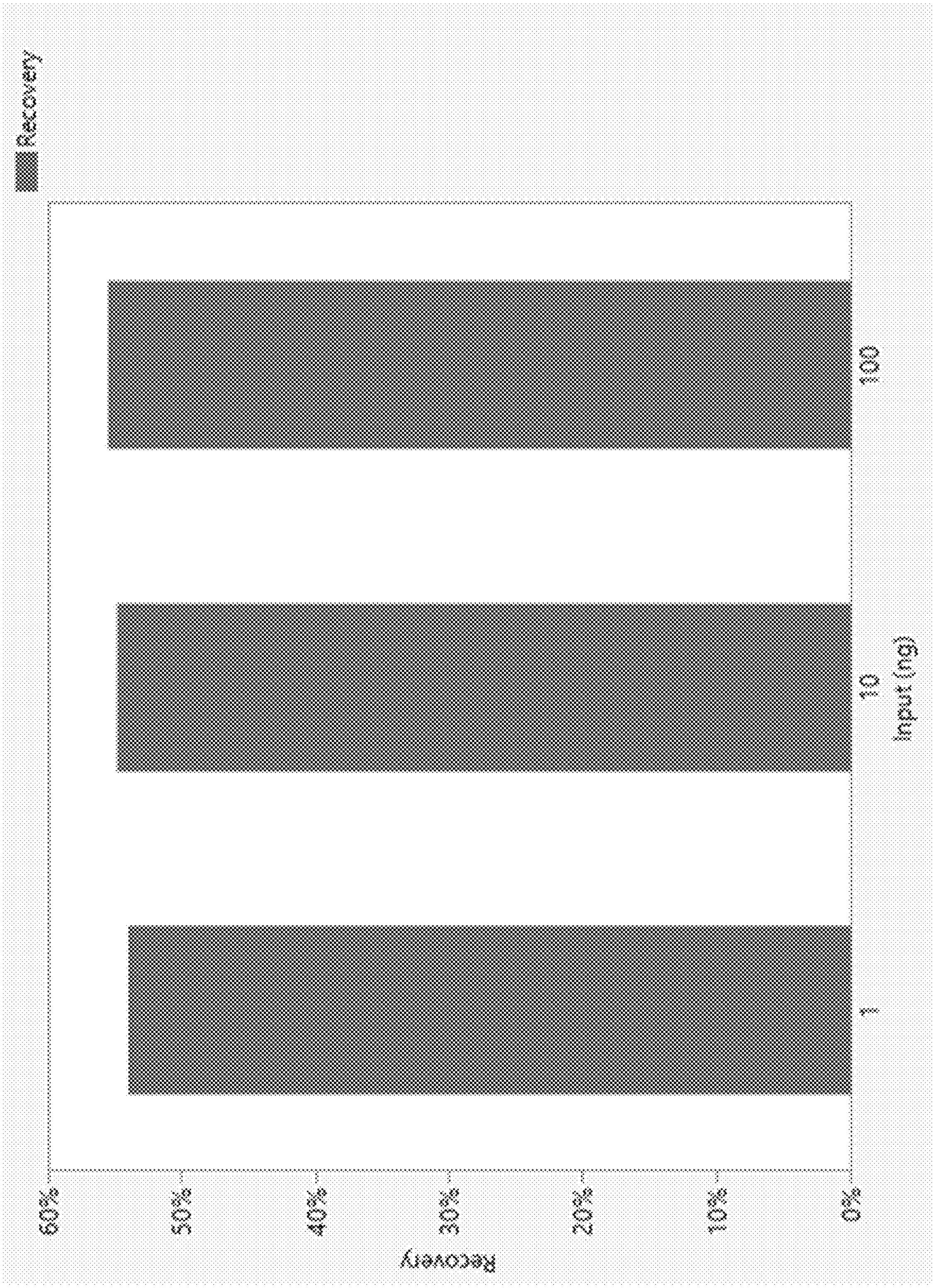
FIG. 6 shows DNA binding percentage and elution percentage from morpholine-functionalized magnetic silica particles, using various DNA input concentrations.

Results are shown in FIG. 6. The morpholine-functionalized beads are able to concentrate total DNA and the subsequent DNA can be utilized in a downstream qPCR reaction.

Example 8

RNA Binding and Elution Assay 1 mg of morpholine functionalized magnetic beads was added into 1 mL of total RNA (1000, 100 or 10 ng) solution of Phosphate Buffered Saline (PBS) pH 7.0. The total RNA used in this assay was isolated from human embryonic kidney 293 cells (commonly referred to as HEK 293, HEK-293 or 293 cells). The suspension was mixed for 60 seconds. The particles were collected by a magnetic bar for 1 minute. The supernatant was removed, 50 μL of Tris buffer (10 mM, pH 9.0) was added into the magnetic particles, and the suspension vortexed for 1 minute. The particles were collected by a magnetic bar. The elution solution was collected, and DNA concentration in the elution solution was quantified using probe-based 1-Step quantitative real-time PCR (RT-qPCR) to calculate the elution concentration. Beta-2-microglobulin probe and primers were used to compare the RNA solution input and the elution concentration.

Figure 7:
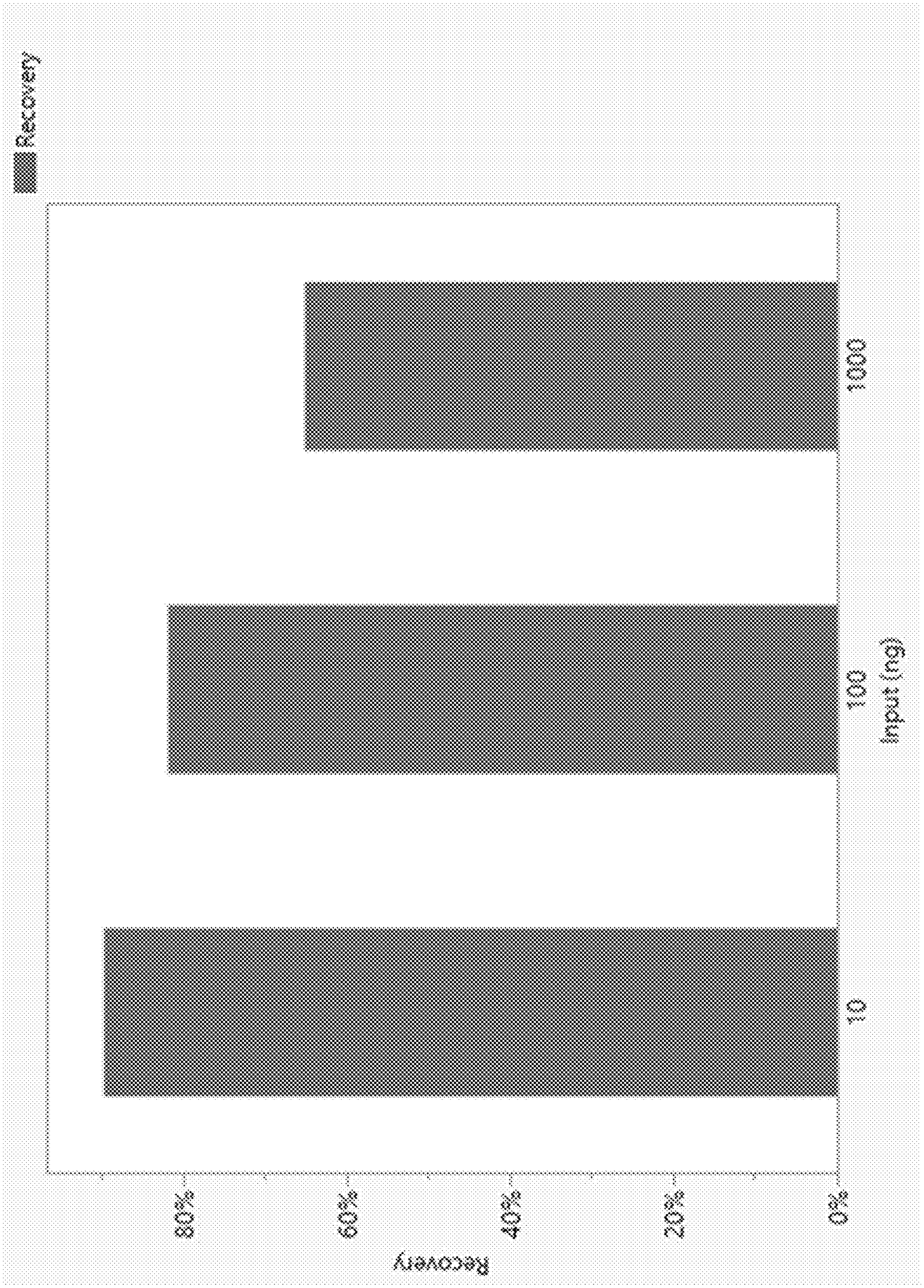
FIG. 7 shows RNA binding percentage and elution percentage from morpholine-functionalized magnetic silica particles, using various RNA input concentrations.

Results are shown in FIG. 7. The morpholine-functionalized beads are able to concentrate total RNA and the subsequent RNA can be utilized in a downstream 1-Step RT-qPCR reaction.

Example 9 ccfDNA (cell-free circulating DNA) was isolated from 1 mL of human blood plasma using the Promega Maxwell Instrument. Method 1 is the current Promega inventory product (#AS1480). Method 2 uses the morpholine functionalized magnetic beads of the present disclosure. Method 2 also included a low pH salt wash after the binding step. Recovered ccfDNA was measured by qPCR.

Figure 8:
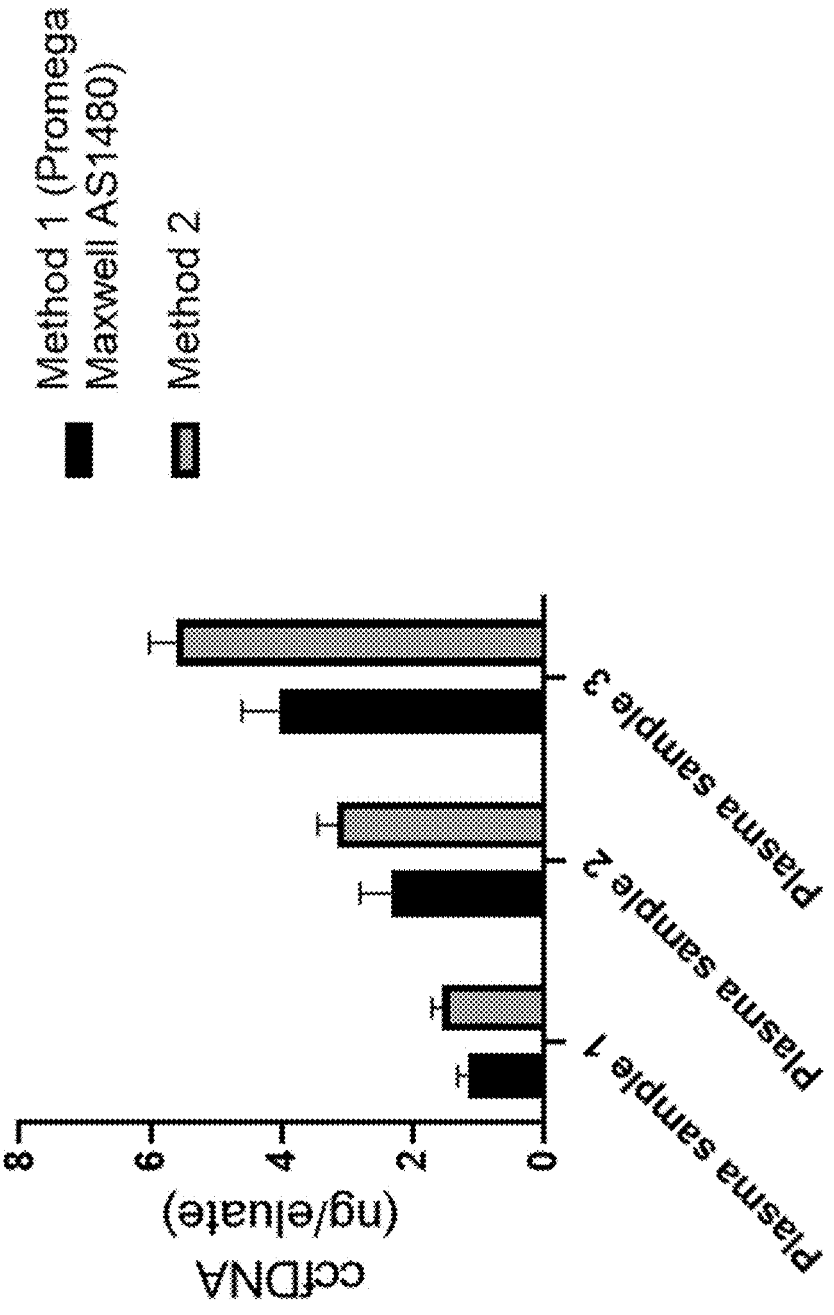
FIG. 8 shows isolation and concentration of ccfDNA (circulating cell-free DNA) using the morpholine-functionalized beads.

Results are shown in FIG. 8. The rapid sample prep chemistry using morpholine-functionalized beads of the present disclosure in method 2 can isolate and concentrate ccfDNA rapidly and with high recovery yield. In all three plasma samples, the rapid sample prep chemistry using morpholine-functionalized beads generated higher yield than commercial Promega Maxwell ccfDNA kit.

The invention claimed is:

1. A composition comprising:

a solid surface;

a linker covalently attached to the solid surface, wherein the linker has a structure:

$$—(CH_2)_{n1}—Z—(CH_2)_{n2}—$$

wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S)NH—, and —O—, and —C(O)O—; and a moiety of formula (I) covalently attached to the linker:

(I)

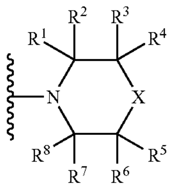

wherein:

X is selected from O, S, S(O), and $S(O)_2$;

$R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, —$NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl.

2. The composition of claim 1, wherein the solid surface comprises a material selected from silica, glass, a polymer, and a metal.

3. The composition of claim 1, wherein the solid surface comprises a polymer selected from cellulose, cellulose acetate, nitrocellulose, nylon, a polyester, a polyethylene, a polyethersulfone, a polyolefin, polyvinylidene fluoride, a polyacrylate, a polystyrene, or any combination thereof.

4. The composition of claim 1, wherein the solid surface is in the form of a bead, a resin, a magnetic particle, a membrane, a vial, a plate, a film, a tube, a syringe, a cartridge, a cassette, a pipette tip, a microfluidic cartridge, or a cuvette.

5. The composition of claim 1, wherein the linker is selected from:

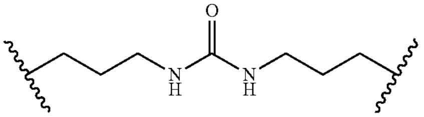

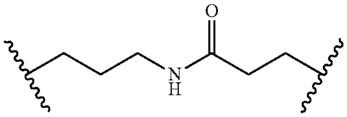

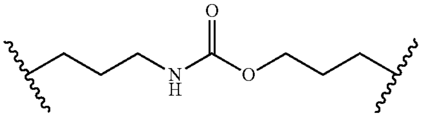

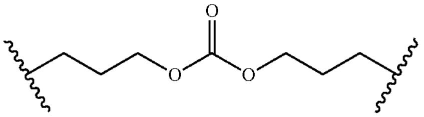

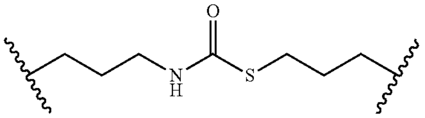

-continued

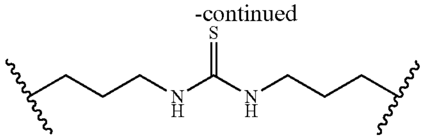

and

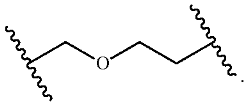

6. The composition of claim 5, wherein the linker is:

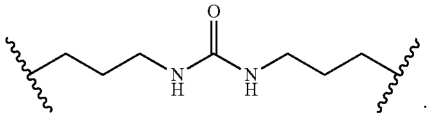 [SMILES: *CCCNC(=O)NCCC*]

7. The composition of claim 1, wherein X is O.

8. The composition of claim 1, wherein $R^1$, $R^2$, $R^3$, $R^4$, $R^5$, $R^6$, $R^7$, and $R^8$ are each hydrogen.

9. The composition of claim 1, wherein the solid surface further comprises one or more additional moieties covalently bound to the surface.

10. The composition of claim 1, wherein the solid surface further comprises at least one polyethylene glycol (PEG) moiety covalently bound to the surface.

11. The composition of claim 1, wherein X is O, and wherein $R^1$, $R^2$, $R^3$, $R^4$, $R^5$, $R^6$, $R^7$, and $R^8$ are each hydrogen.

12. A method of isolating a nucleic acid from a sample, comprising:

(a) providing a sample containing a nucleic acid;

(b) contacting the sample with a composition comprising:

a solid surface;

a linker covalently attached to the solid surface, wherein the linker has a structure:

$$—(CH_2)_{n1}—Z—(CH_2)_{n2}—$$

wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S)NH—, —O—, and —C(O)O—; and a moiety of formula (I) covalently attached to the linker:

(I)

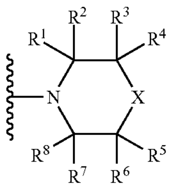

wherein:

X is selected from O, S, S(O), and $S(O)_2$; and $R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, —$NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl;

at a pH of less than about 8.0, wherein the nucleic acid binds to the composition to provide a nucleic acid bound composition; and (c) separating the nucleic acid bound composition from the sample.

13. The method of claim 12, wherein step (b) is conducted at a pH of about 2.0 to less than about 8.0.

14. The method of claim 12, wherein step (b) comprises contacting the sample with the composition for about 10 seconds to about 10 minutes.

15. The method of claim 12, further comprising one or more steps of washing the nucleic acid bound composition after step (c) by contacting the composition with a wash solution having a pH of less than about 8.0.

16. The method of claim 12, further comprising a step of contacting the nucleic acid bound composition with an elution solution at a pH of about 8.5 or higher, to release the nucleic acid from the composition.

17. The method of claim 12, wherein the nucleic acid is DNA, and the DNA is selected from total DNA, mtDNA (mitochondrial DNA), gDNA (genomic DNA), cfDNA (cell-free DNA), ccfDNA (circulating cell-free DNA), cffDNA (cell free fetal DNA), bacterial DNA, viral DNA, and ctDNA (circulating tumor DNA).

18. The method of claim 12, wherein the nucleic acid is RNA, and the RNA is selected from total RNA, miRNA, mRNA, tRNA, rRNA, siRNA, ctRNA (circulating tumor RNA), and viral RNA.

19. A compound of formula (IIa):

(IIa)

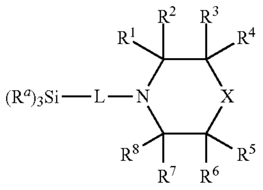

or a salt thereof, wherein:

X is selected from O, S, S(O), and $S(O)_2$;

L is a linker, wherein the linker has a structure:

$$—(CH_2)_{n1}—Z—(CH_2)_{n2}—$$

wherein n1 and n2 are each independently selected from 1, 2, 3, 4, 5, 6, 7, and 8, and Z is selected from —NHC(O)NH—, —C(O)NH—, —OC(O)NH—, —OC(O)O—, —NHC(O)S—, —NHC(S) NH—, —O—, and —C(O)O—;

each $R^a$ is independently selected from hydroxy, $C_1$-$C_6$ alkoxy, and halo; and $R^1$, $R^2$, $R^3$, $R^4$, $R^5$, $R^6$, $R^7$, and $R^8$ are each independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, aryl, heteroaryl, heterocyclyl, halo, cyano, nitro, —$OR^a$, —$SR^b$, —$C(O)OR^c$, —$C(O)NR^dR^e$, —$OC(O)NR^fR^g$, $NR^hC(O)NR^iR^j$, and —$NR^hC(S)NR^iR^j$, wherein each $R^a$, $R^b$, $R^c$, $R^d$, $R^e$, $R^f$, $R^g$, $R^h$, $R^i$, and $R^j$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, and aryl.

20. The compound of claim 19, wherein the compound is:
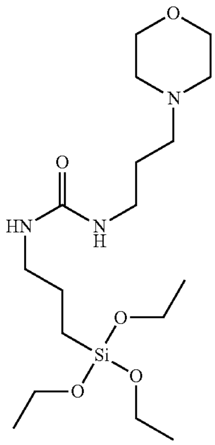
,
or a salt thereof.
* * * * *